United States Patent [19]
Goldsteen et al.

[11] Patent Number: 5,941,908
[45] Date of Patent: Aug. 24, 1999

[54] ARTIFICIAL MEDICAL GRAFT WITH A RELEASABLE RETAINER

[75] Inventors: David S. Goldsteen, Minneapolis; Thomas J. Bachinski, Lakeville; Daniel J. Sullivan, Medina, all of Minn.

[73] Assignee: Vascular Science, Inc., Minneapolis, Minn.

[21] Appl. No.: 08/844,979

[22] Filed: Apr. 23, 1997

[51] Int. Cl.⁶ .................................................. A61F 2/06
[52] U.S. Cl. ........................... 623/1; 623/12; 606/153; 606/198
[58] Field of Search ..................... 623/1, 12; 606/153, 606/195, 198

[56] References Cited

U.S. PATENT DOCUMENTS

| | | | |
|---|---|---|---|
| 4,214,587 | 7/1980 | Sakura, Jr. ............................ | 128/334 |
| 4,418,693 | 12/1983 | LeVeen et al. ....................... | 128/303 |
| 4,459,252 | 7/1984 | MacGregor ........................... | 264/46.9 |
| 4,487,567 | 12/1984 | Possis et al. ......................... | 425/403 |
| 4,503,569 | 3/1985 | Dotter ................................... | 3/1.4 |
| 4,546,499 | 10/1985 | Possis et al. ......................... | 623/1 |
| 4,562,597 | 1/1986 | Possis et al. ......................... | 623/1 |
| 4,592,754 | 6/1986 | Gupte et al. .......................... | 623/1 |
| 4,601,718 | 7/1986 | Possis et al. ......................... | 623/1 |
| 4,605,406 | 8/1986 | Cahalan et al. ....................... | 623/1 |
| 4,617,932 | 10/1986 | Kornberg ............................. | 128/334 |
| 4,629,458 | 12/1986 | Pinchuk ................................ | 623/1 |
| 4,632,842 | 12/1986 | Karwoski et al. .................... | 427/2 |
| 4,657,544 | 4/1987 | Pinchuk ................................ | 623/1 |
| 4,665,906 | 5/1987 | Jervis ................................... | 128/92 |
| 4,718,907 | 1/1988 | Karwoski et al. .................... | 623/12 |
| 4,733,665 | 3/1988 | Palmaz ................................. | 128/343 |
| 4,738,740 | 4/1988 | Pinchuk et al. ...................... | 156/167 |
| 4,743,252 | 5/1988 | Martin, Jr. et al. ................... | 623/1 |
| 4,759,757 | 7/1988 | Pinchuk ................................ | 623/1 |
| 4,787,899 | 11/1988 | Lazarus ................................ | 623/1 |
| 4,798,606 | 1/1989 | Pinchuk ................................ | 623/1 |
| 4,892,539 | 1/1990 | Koch .................................... | 623/1 |
| 4,909,979 | 3/1990 | Possis et al. ......................... | 264/571 |

(List continued on next page.)

FOREIGN PATENT DOCUMENTS

| | | |
|---|---|---|
| 670239 | 7/1996 | Australia . |
| 0 539 237 A1 | 4/1993 | European Pat. Off. . |
| 0 637 454 A1 | 2/1995 | European Pat. Off. . |
| 0 680 734 A2 | 11/1995 | European Pat. Off. . |
| 0 684 022 A2 | 11/1995 | European Pat. Off. . |
| 0 712 614 A1 | 5/1996 | European Pat. Off. . |
| 2 269 104 | 2/1994 | United Kingdom . |
| WO 93/00868 | 1/1993 | WIPO . |
| WO 94/06372 | 3/1994 | WIPO . |
| WO 96/01591 | 1/1996 | WIPO . |
| WO 96/01599 | 1/1996 | WIPO . |
| WO 96/14808 | 5/1996 | WIPO . |
| WO 96/18361 | 6/1996 | WIPO . |
| WO 96/22745 | 8/1996 | WIPO . |

*Primary Examiner*—Paul B. Prebilic
*Attorney, Agent, or Firm*—Fish & Neave; Robert R. Jackson; Walter M. Egbert, III

[57] ABSTRACT

A tubular artificial graft for attachment to a patient's tubular body tissue has an initially radially relatively small connector structure adjacent each of its ends. The initial relatively small size of each connector structure facilitates insertion of that portion of the graft into the body tissue to which that connector structure is to make a connection. After a connector structure is properly positioned relative to the body tissue, the connector structure is radially enlarged to connect the graft to the body tissue. The connection is preferably both a mechanical and a fluid-tight connection.

15 Claims, 3 Drawing Sheets

U.S. PATENT DOCUMENTS

| | | | |
|---|---|---|---|
| 4,955,899 | 9/1990 | Della Corna et al. | 623/901 |
| 5,037,377 | 8/1991 | Alonso | 600/36 |
| 5,061,275 | 10/1991 | Wallsten et al. | 623/1 |
| 5,084,065 | 1/1992 | Weldon et al. | 623/1 |
| 5,100,422 | 3/1992 | Berguer et al. | 606/151 |
| 5,104,399 | 4/1992 | Lazarus | 623/1 |
| 5,104,400 | 4/1992 | Berguer et al. | 264/132 |
| 5,116,360 | 5/1992 | Pinchuk et al. | 623/1 |
| 5,122,154 | 6/1992 | Rhodes | 606/198 |
| 5,135,467 | 8/1992 | Citron | 600/16 |
| 5,152,782 | 10/1992 | Kowligi et al. | 623/1 |
| 5,163,951 | 11/1992 | Pinchuk et al. | 623/1 |
| 5,211,658 | 5/1993 | Clouse | 623/1 |
| 5,211,683 | 5/1993 | Maginot | 128/898 |
| 5,246,451 | 9/1993 | Trescony et al. | 623/1 |
| 5,246,452 | 9/1993 | Sinnott | 623/1 |
| 5,275,622 | 1/1994 | Lazarus et al. | 623/1 |
| 5,282,847 | 2/1994 | Trescony et al. | 623/1 |
| 5,304,220 | 4/1994 | Maginot | 623/1 |
| 5,306,240 | 4/1994 | Berry | 604/51 |
| 5,316,023 | 5/1994 | Palmaz et al. | 128/898 |
| 5,360,443 | 11/1994 | Barone et al. | 623/1 |
| 5,366,504 | 11/1994 | Andersen et al. | 623/11 |
| 5,387,235 | 2/1995 | Chuter | 623/1 |
| 5,397,345 | 3/1995 | Lazarus | 623/1 |
| 5,413,598 | 5/1995 | Moreland | 623/1 |
| 5,425,765 | 6/1995 | Tiefenbrun et al. | 623/12 |
| 5,429,144 | 7/1995 | Wilk | 128/898 |
| 5,443,497 | 8/1995 | Venbrux | 623/1 |
| 5,443,499 | 8/1995 | Schmidt | 623/1 |
| 5,452,733 | 9/1995 | Sterman et al. | 128/898 |
| 5,456,712 | 10/1995 | Maginot | 623/1 |
| 5,489,295 | 2/1996 | Piplani et al. | 623/1 |
| 5,496,364 | 3/1996 | Schmitt | 623/1 |
| 5,496,365 | 3/1996 | Sgro | 623/1 |
| 5,507,769 | 4/1996 | Marin et al. | 606/198 |
| 5,509,931 | 4/1996 | Schmitt | 623/1 |
| 5,522,880 | 6/1996 | Barone et al. | 623/1 |
| 5,527,355 | 6/1996 | Ahn | 623/12 |
| 5,562,725 | 10/1996 | Schmitt et al. | 623/1 |
| 5,584,875 | 12/1996 | Duhamel et al. | 623/1 |
| 5,584,876 | 12/1996 | Bruchman et al. | 623/1 |
| 5,607,463 | 3/1997 | Schwartz et al. | 623/1 |
| 5,607,464 | 3/1997 | Trescony et al. | 623/1 |
| 5,609,624 | 3/1997 | Kalis | 623/1 |
| 5,628,782 | 5/1997 | Myers et al. | 623/1 |
| 5,628,786 | 5/1997 | Banas et al. | 623/1 |
| 5,628,788 | 5/1997 | Pinchuk | 623/1 |
| 5,632,772 | 5/1997 | Alcime et al. | 623/1 |
| 5,653,747 | 8/1997 | Dereume | 623/1 |
| 5,665,117 | 9/1997 | Rhodes | 623/1 |
| 5,676,670 | 10/1997 | Kim | 606/108 |

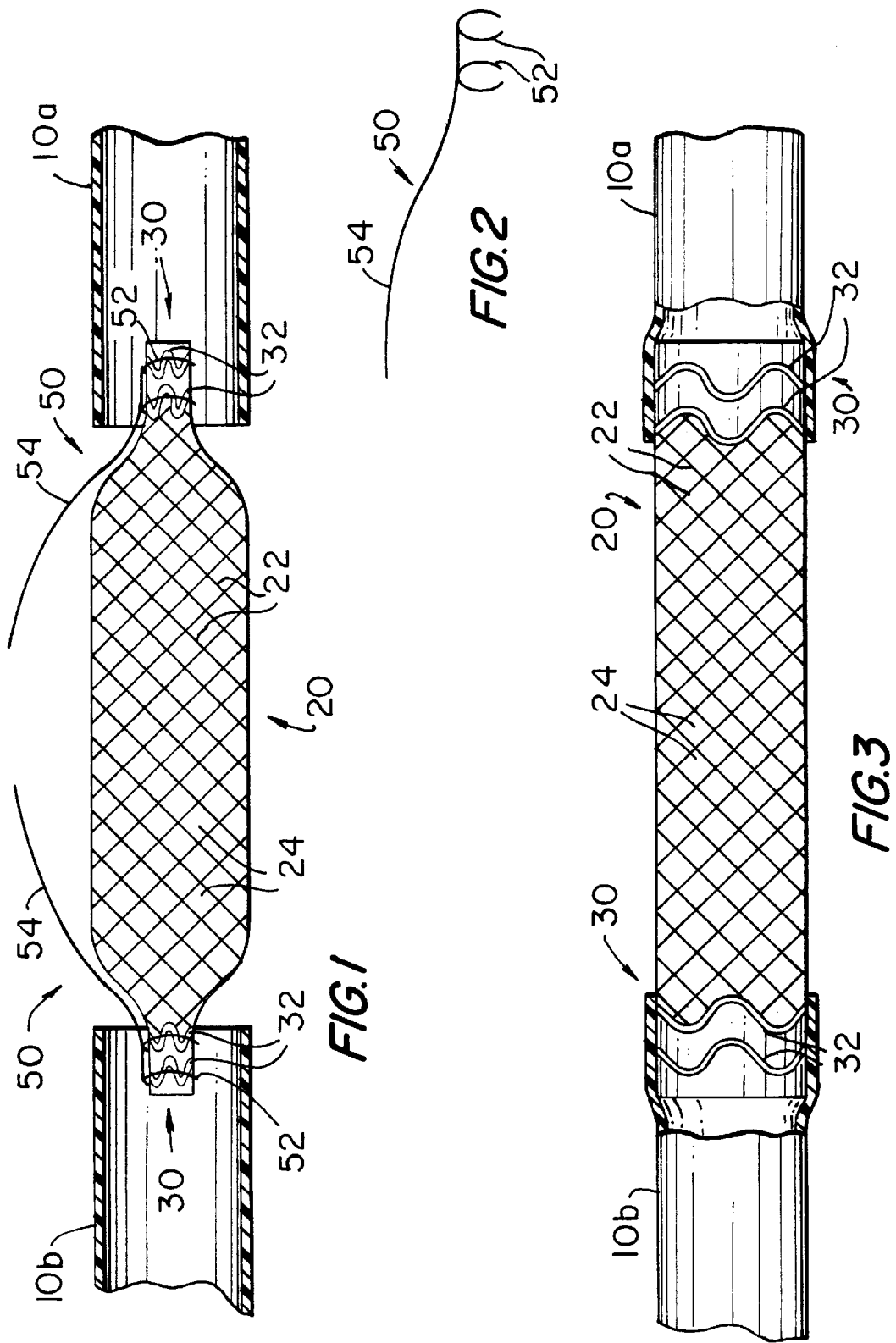

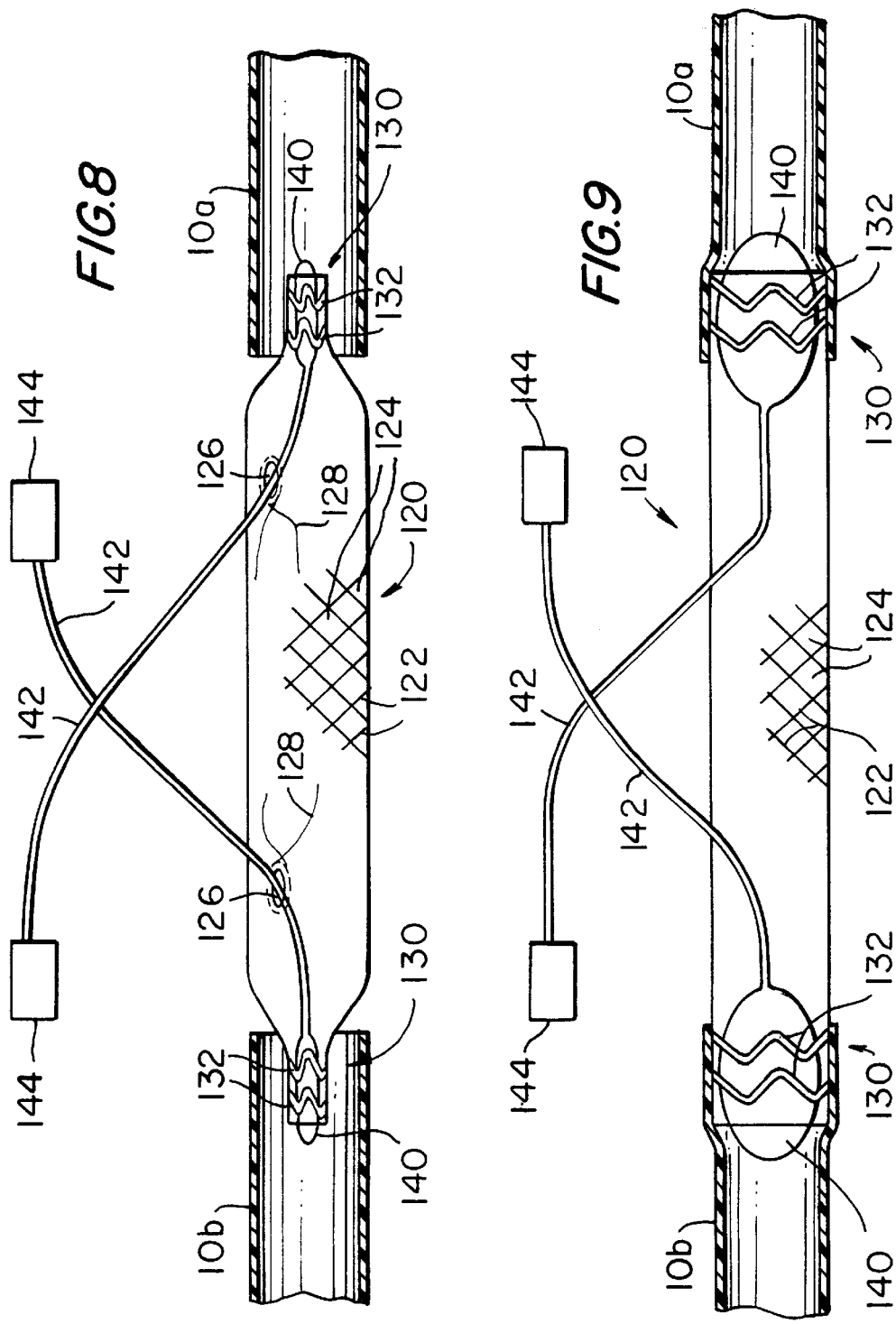

ARTIFICIAL MEDICAL GRAFT WITH A RELEASABLE RETAINER

BACKGROUND OF THE INVENTION

This invention relates to medical apparatus and procedures, and more particularly to artificial medical graft methods and apparatus.

Tubular artificial grafts are needed in various medical procedures. For example, such grafts may be needed to replace diseased or damaged sections of natural tubular body tissue such as in the circulatory system, the urinary tract, etc. Or such grafts may be needed to make new connections in natural tubular body tissue systems such as bypass or shunt connections in the circulatory system. An artificial tubular graft may be needed as either a temporary or permanent installation.

Important considerations regarding the use of artificial grafts include ease of use, time required for installation, secureness of installation, and performance after installation. Improvements are constantly sought in all of these areas.

In view of the foregoing, it is an object of this invention to provide improved artificial grafts.

It is another object of this invention to provide improved methods and apparatus for installing medical grafts.

SUMMARY OF THE INVENTION

These and other objects of the invention are accomplished in accordance with the principles of the invention by providing artificial tubular grafts that have axial end portions that are initially radially relatively small, but that can be radially enlarged when desired. In their initially radially relatively small condition, the axial end portions of the graft are easily inserted into the ends of or other apertures in the natural body tissue tubes to be connected. Once each axial end portion of the graft is properly positioned in the appropriate natural body tissue tube, that end portion is radially enlarged to securely engage the tissue tube. In addition to providing mechanical attachment of the artificial graft to the body tissue tube, the radial enlargement of the graft end portions provides a fluid-tight seal between the graft and the body tissue tubes. Various techniques may be used for radially expanding the end portions of the graft. The graft may be augmented with various types of connectors or fasteners for helping to ensure good mechanical and fluid-tight connection between the graft and the body tissue.

Further features of the invention, its nature, and various advantages will be more apparent from the accompanying drawings and the following detailed description of the preferred embodiments.

BRIEF DESCRIPTION OF THE DRAWINGS

FIG. 1 is a simplified elevational view of an illustrative embodiment of an artificial graft and illustrative apparatus useful in installing the graft, all in accordance with this invention. FIG. 1 shows the graft being installed between the ends of two sections of natural body tissue tubing.

FIG. 2 is a simplified elevational view of an illustrative embodiment of a portion of the apparatus shown in FIG. 1.

FIG. 3 is a view similar to FIG. 1 showing the installed graft.

FIG. 8 is another view generally similar to FIG. 1, but showing another illustrative embodiment of the invention.

FIG. 9 is a view similar to FIG. 8 showing a later stage in use of the FIG. 8 apparatus.

DETAILED DESCRIPTION OF THE PREFERRED EMBODIMENTS

Figure 5:
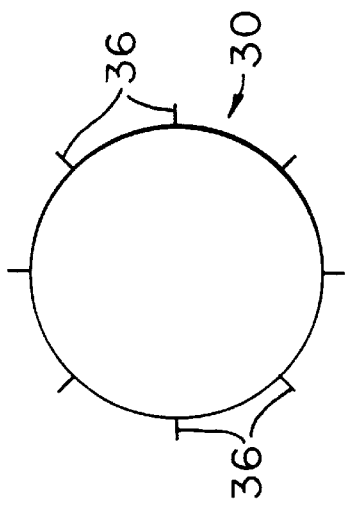
FIG. 5 is a simplified end view of another illustrative embodiment of a portion of the apparatus shown in FIG. 3.

In the illustrative embodiment shown in FIG. 1, artificial tubular graft 20 is being installed between the ends of two sections 10a and 10b of natural body tissue tubing in a patient. For example, the purpose of graft 20 may be to replace a diseased or damaged portion of the patient's body tissue tubing that has been removed. Tubing 10 may be circulatory system tubing or any other body tissue tubing that is suitable for use with graft 20.

Although any suitable construction can be used for the main portion of graft 20, a particularly preferred construction is shown and described in Goldsteen et al. U.S. patent application Ser. No. 08/745,618, filed Nov. 7, 1996, which is hereby incorporated by reference herein in its entirety. For example, this graft construction may include a tubular mesh framework 22 of nitinol covered with silicone 24 to substantially fill in the interstices in the framework. Additional details, features, and alternatives regarding this type of graft construction will be found in the above-mentioned Goldsteen et al. reference, and in Bachinski et al. U.S. patent application Ser. No. 08/839,080, filed Apr. 23, 1997, which is also hereby incorporated by reference herein in its entirety. For present purposes, it will be sufficient to point out that grafts having this type of construction are extremely elastic and that they can be radically deformed without damage or permanent change in shape. They can be made with any desired porosity (e.g., through the silicone). For use in the circulatory system, they can also be made so that they pulse in response to pressure pulses in the blood flowing through them, very much like the pulsation of natural blood vessels. This can be important to discouraging the formation of clots in the graft.

In accordance with the present invention, each axial end portion of graft 20 includes a radially enlargeable connector structure 30. In embodiments of the type shown in FIG. 1, each connector structure 30 is self-expanding. In other words, each connector structure 30 is an elastic, annular structure which is resiliently biased to return to a radially enlarged size that is preferably at least as large as (and more preferably somewhat larger than) the body tissue tube opening to which that end portion of the graft will be attached. Initially, however, each connector structure 30 is radially compressed to a substantially smaller size as shown in FIG. 1. This allows each axial end portion of graft 20 to be easily inserted (as shown in FIG. 1) into the body tissue tubing 10 to which that end portion of the graft is to be attached.

In the particular embodiment shown in FIG. 1, the initial radial compression of each connector structure 30 is maintained by a clip structure 50 on that connector structure. Each clip structure 50 includes a clip portion 52 and a release portion 54 (see also FIG. 2). For example, each clip structure 50 may be made of stainless steel, with the clip portion 52 being strong enough to radially compress the associated connector structure 30. However, when the release portion 54 of either clip structure 50 is pulled radially out from graft 20, the C-shaped clip portion 52 of that clip structure comes off the associated connector structure 30. This allows the associated connector structure to resiliently radially expand into firm contact with the inner surface of the surrounding body tissue tubing 10 as shown in FIG. 3. This firm contact provides a fluid-tight seal between body tissue 10 and graft 20, as well as secure mechanical attachment of the graft to the tissue.

As an alternative to depicted clip structures 50, each connector structure 30 may be initially radially compressed by a wire wrapped around the connector structure. When it is desired to radially enlarge the connector structure, the wire is unwrapped from that structure.

Many other types of removable retaining structures are possible as alternatives to clip structures 50 or the above-mentioned wire wrapping for initially radially compressing connector structures 30. For example, spring-loaded clamps can be used, and such clamps can be provided with lever-type opening arms, or such clamps can be adapted for opening with a pliers-type or forceps-type instrument.

Figure 4:
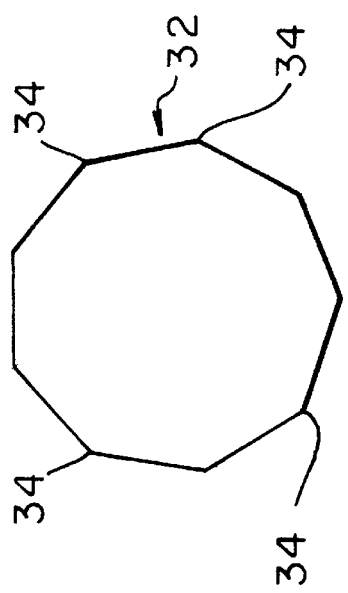
FIG. 4 is a simplified end view of an illustrative embodiment of a portion of the apparatus shown in FIG. 3.

Connector structures 30 may have any of a large number of constructions. For example, each connector structure 30 may include one or more annularly compressible, serpentine-shaped, metal rings 32 (e.g., of nitinol). When such a ring is annularly compressed (e.g., as shown in FIG. 1), the serpentine convolutions of the ring become more sharply curved and closer together). When such a ring is released to return to a more nearly relaxed state, the convolutions of the ring become somewhat straighter. If graft 20 is made of a metal (e.g., nitinol) framework 22 with a covering 24 (e.g., of silicone), rings 32 may be integral with framework 22, and covering 24 may continue into the vicinity of rings 32. Rings 32 may be formed to press substantially uniformly out against the inner surface of body tissue tubing 10 all the way around the circumference of the graft. Alternatively, rings 32 may be formed with circumferentially spaced "high spots" or "pressure points" 34 (see FIG. 4) which locally bear somewhat more strongly on the inner surface of body tissue tubing 10. Such localized points 34 of higher bearing pressure and therefore greater indentation of body tissue tubing 10 can help ensure that the end portion of the graft does not slip out of the body tubing after the graft has been installed.

Any construction of connector structures 30 may additionally include structures 36 (see FIG. 5) which radially penetrate the adjacent body tissue tubing 10. If such tissue-piercing structures 36 are provided, they may be substantially straight prongs or struts, curved hooks, or any other suitably shaped members. If provided, structures 36 may be sharply pointed to facilitate tissue penetration, and they may be barbed (e.g., like fishing hooks) to substantially prevent them from coming out of the tissue they have pierced.

Figure 7:
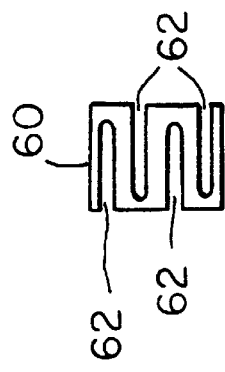
FIG. 7 is a simplified elevational view of a subsequent condition of the FIG. 6 structure during fabrication.
Figure 6:
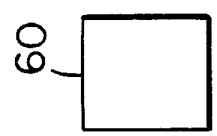
FIG. 6 is an elevational view of a structure that can be used to make a particular embodiment of the apparatus portion shown in FIG. 4.

A particularly preferred way of producing a serpentine ring 32 with the above-described high spots 34 is to start with a short length of thin-walled metal tubing 60 as shown in FIG. 6 and cut away interdigitated portions 62 from opposite axial ends of the tube as shown in FIG. 7. The resulting structure is then radially enlarged and annealed. In its radially enlarged form, the structure has the general appearance shown in FIG. 4 when viewed from an axial end. Each point 34 is adjacent an axial end of the original tube 60. The structure can be resiliently radially compressed to the size of the original tube 60 or an even smaller size, and it will return to the radially enlarged size and shape whenever released from radial compression.

In the alternative embodiment shown in FIG. 8 each connector structure 130 contains a dilatation balloon 140 connected to an associated inflation device 144 by an associated tube 142. (Elements in the FIG. 8 embodiment that are the same as or similar to elements in the previously described embodiments have reference numbers that are increased by 100 from the reference numbers used for the corresponding elements in the previously described embodiments.) Each of tubes 142 may pass through an aperture 126 in the side wall of tubular graft 120. Each of apertures 126 may be provided with a purse string suture 128 or other functionally equivalent structure for use in closing the aperture when desired.

Balloons 140 are initially uninflated so that connector structures 130 can be initially radially relatively small as shown in FIG. 8. As in the case of FIG. 1, the initially relatively small radial size of connector structures 130 facilitates their insertion in the body tissue tubing 10a and 10b to which graft 120 is to be attached. Each connector structure 130 may be a structure which is plastically deformable to a radially relatively large size by inflation of the associated balloon 140. Alternatively, each connector structure 130 may be a radially compressed, self-expanding structure that is releasably held in a radially compressed state by an associated frangible structure. When additional radial enlarging force is exerted by inflation of the associated balloon 140, the frangible structure breaks and the connector structure 130 returns resiliently to a radially enlarged size.

FIG. 9 shows inflation of balloons 140 to radially enlarge connector structures 130, either by plastically deforming the connector structures or by releasing the connector structures from frangible or other similar restraints. When radially enlarged as shown in FIG. 9, connector structures 130 engage the surrounding body tissue 10 and form a fluid-tight seal and mechanical attachment between the body tissue and graft 120. Connector structures 130 may have any of the constructions and/or features described above in connection with structures 30 (e.g., with reference to FIGS. 4–7) for helping to ensure good mechanical and fluid-tight connections between body tissue 10 and graft 120.

After graft 120 has been installed by inflation of balloons 140 as shown in FIG. 9, balloons 140 are deflated again. Then tubes 142 and balloons 140 are withdrawn from graft 120 via apertures 126. After apertures 126 have thus been cleared, apertures 126 are closed (e.g., by tightening and securing purse string sutures 128). Except for the addition of closed apertures 126, the appearance of finished and fully installed graft 120 may be substantially as shown for graft 20 in FIG. 3.

Grafts 20/120 are preferably made up in a range of sizes (e.g., lengths and diameters) so that they are available for various patient applications. Grafts 20/120 may also be made in a variety of shapes, and these various shapes may also be made in a range of sizes. For example, grafts 20/120 may be made in curved shapes, Y shapes, T shapes, etc. In the case of shapes with more than two ports (e.g., Y or T shapes with three ports), each port is provided with a connector structure 30/130 for attachment of that port to body tissue of the patient. References to "tubular grafts" herein include such graft structures with more than two ports. References herein to "ends" or "end portions" of grafts refer to the port regions of grafts, regardless of the shape or number of ports of the graft.

It will be understood that the foregoing is only illustrative of the principles of this invention and that various modifications can be made by those skilled in the art without departing from the scope and spirit of the invention. For example, the number of rings 32 used in each of connector structures 30/130 can differ from the number employed in the embodiments shown herein. Other possible constructions or features of connector structures 30/130 are shown in Bachinski et al. U.S. patent application Ser. No. 08/839,080, filed Apr. 23, 1997, which is hereby incorporated by reference herein in its entirety. In embodiments of the type shown in FIGS. 8 and 9, structures other than balloons 140 may be used for radially enlarging connector structures 130. For example, a radially enlargeable mechanical structure somewhat like a reversely operating pair of pliers or a reversely operating forceps may be used inside each connector structure 130 to radially enlarge the connector structure. Although illustrative grafts 20/120 are shown connecting ends of body tissue tubing 10, it will be understood that the grafts of this invention are equally useful in making connections to body tissue tubing through apertures (e.g., incisions) in the side walls of body tissue tubing.

The invention claimed is:

1. A graft system comprising:

a tubular graft comprising a tubular connection portion which is initially radially relatively small and which is selectively radially enlargeable, the connection portion being configured to selectively resiliently radially enlarge from being radially relatively small; and a releasable retainer configured to retain the connection portion radially relatively small until the retainer releases the connection portion, the retainer comprising a removable structure disposed at least part way around the connector portion, the removable structure comprising a C-shaped clip structure.

2. The graft system defined in claim 1 wherein the connection portion comprises:

an initially radially compressed annular structure.

3. The graft system defined in claim 2 wherein the annular structure is serpentine-shaped in the annular direction.

4. The graft system defined in claim 3 wherein the annular structure is radially compressed at least in part by increasing the curvature of the serpentine shape.

5. The graft system defined in claim 2 wherein the annular structure comprises a plurality of projecting portions which project radially outward beyond the remainder of the annular structure at least when the connection portion is radially enlarged.

6. The graft system defined in claim 5 wherein the projecting portions are configured to penetrate body tissue to which the graft is connected.

7. The graft system defined in claim 2 wherein the annular structure is formed from a tube from which interdigitated portions that extend in from the axial ends of the tube have been removed.

8. A graft system comprising:

a tubular graft comprising a tubular connection portion which is initially radially relatively small and which is selectively radially enlargeable;

a selectively radially enlargeable structure for selectively radially enlarging the connection portion, wherein the radially enlargeable structure is controlled via a control structure which passes through an aperture in a tubular side wall of the graft, and the radially enlargeable structure and the control structure are configured to be withdrawn via the aperture; and a structure configured to selectively close the aperture.

9. The graft system defined in claim 1 wherein the connection portion comprises:

a plurality of projecting portions which project radially outward beyond the remainder of the connection portion at least when the connection portion is radially enlarged.

10. The graft system defined in claim 9 wherein the projecting portions are configured to penetrate body tissue to which the graft is connected.

11. The graft system defined in claim 4 wherein the annular structure is radially enlarged at least in part by decreasing the curvature of the serpentine shape.

12. The graft system defined in claim 1 further comprising:

a tubular framework extending axially from the connection portion; and a covering on the tubular framework.

13. The graft system defined in claim 12 wherein the framework comprises:

a metal mesh.

14. The graft system defined in claim 13 wherein the metal comprises nitinol.

15. The graft system defined in claim 12 wherein the covering comprises silicone.

* * * * *